United States Patent [19]

Marans et al.

[11] Patent Number: 4,910,340

[45] Date of Patent: Mar. 20, 1990

[54] CATALYTIC METHOD FOR PREPARING SYMMETRICAL AND NONSYMMETRICAL DIALKYLHYDROXYLAMINES

[75] Inventors: Nelson S. Marans, Silver Spring; Stephen G. Harsy, Mt. Airy; Herbert S. Harris, Severn, all of Md.

[73] Assignee: W. R. Grace & Co.-Conn., New York, N.Y.

[21] Appl. No.: 133,119

[22] Filed: Dec. 14, 1987

[51] Int. Cl.$^4$ .................. C07C 83/00; C07C 79/04
[52] U.S. Cl. ................... 564/301; 564/300; 568/943
[58] Field of Search .................. 564/300, 301

[56] References Cited

U.S. PATENT DOCUMENTS

| | | | |
|---|---|---|---|
| 3,178,467 | 4/1966 | Gerjovich et al. | 564/301 X |
| 3,422,144 | 1/1969 | Hoffmann et al. | 564/300 |
| 3,839,449 | 10/1974 | Herold | 564/301 X |
| 4,067,690 | 3/1978 | Cuisia et al. | 21/2.7 R |
| 4,350,606 | 8/1982 | Cuisia et al. | 252/392 |

OTHER PUBLICATIONS

Millan et al., "A Shorter Sidgwick Organic Chemistry of Nitrogen", pp. 240–241 (1969).
Vavon et al., Hydrogenation of Nitrobenzene with Platinum Black, Chem. Abs. 22, 4502 (1928).
Emmons, Wm. D., Preparation and Properties of Oxaziranes, J.A.C.S. 79, 5739 (1957).
Horner et al., Notiz ueber Darstellung und Eigenschaften Einiger Isonitrone (Oxazirane), Chem. Ber. 90, 2184 (1957).
Cope et al., Rearrangement of Oxime N-Ethers, J.A.C.S. 72, 4896 (1950).
Hamer et al., Nitrones, Chem. Rev. 64, 473 (1964).

*Primary Examiner*—Robert V. Hines
*Attorney, Agent, or Firm*—Howard J. Troffkin

[57] ABSTRACT

A process of forming N,N-dialkylhydroxylamines (a class of compounds useful as oxygen scavengers in boiler water feed) by contacting an N-alkylhydroxylamine with an alkyl carbonyl compound to form a nitrone in situ or, alternatively, using previously formed alkylnitrone which is subjected to $H_2$ and a hydrogenation catalyst.

8 Claims, No Drawings

CATALYTIC METHOD FOR PREPARING SYMMETRICAL AND NONSYMMETRICAL DIALKYLHYDROXYLAMINES

BACKGROUND OF THE INVENTION

This invention relates to the preparation of symmetrical and nonsymmetrical N,N-dialkylhydroxylamines from a nitrone. The nitrone reactant can be previously formed or, in the instant process, can be formed in situ without interfering with the eventual formation of the desired hydroxylamines.

Formation of nitrones by the reaction of an N-alkylhydroxylamine with an aldehyde or ketone is known according to the following reaction:

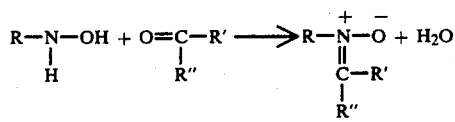

However, according to the literature, results in nitrone reduction are irregular and unpredictable. In certain instances aromatic nitrones have been reduced to the corresponding hydroxylamine. Vavon et al., C.A. 22,4502 (1928) referencing Cusmano, Gazz Chim Ital. 51, II, 306-9 (1921), report that PhN(:O):CHPh can be reduced to the hydroxylamine using $H_2$ and Pt black. Similarly, Horner et al., Chem. Ber. 90, 2184 (1957) discloses that the nitrone PhCH=N(:O)-cyclohexyl was reduced with $H_2$ and Pt black to give the corresponding hydroxylamine, but the reaction required three days to provide the product. Although the aromatic nitrones are known to undergo reduction, the aliphatic derivatives are believed hard to reduce and give results which are unpredictable. For example, according to Hamer et al., Chem. Rev., 64, 491 (1964) which in turn references J.A.C.S. 72, 4896 (1950) certain nitrones when treated with $H_2$ and Raney nickel at atmospheric pressure and room temperature produced moderate yields of imine product and no hydroxylamine in the reaction product. When other reductive agents are used, such as $LiAlH_4$, the nitrone substrate has formed the amine [see W. D. Emmons, J.A.C.S. 79, 5739 (1957)], not the hydroxylamine presently desired.

It will be noted that the prior art shows that reduction of the alkyl nitrone gives amines or, when using Raney catalysts, the imine. In both cases, under the conditions described below, one achieves the N,N-dialkylhydroxylamine. Thus the prior art evidently offers no guide as to results to be predicted from the use of any particular class of nitrone with any particular class of reducing agent.

It is highly desired to form N,N-dialkylhydroxylamines, a known class of compounds useful as oxygen scavengers in boiler feed water treatment, as described in U.S. Pat. No. 4,067,690 to Cuisia et al. It is further highly desired to have a means of forming the desired compounds using a single reaction vessel and also from the more stable (in comparison to the nitrone) N-alkylhydroxylamine.

SUMMARY OF THE INVENTION

The desired N,N-dialkylhydroxylamine can be prepared from the N-alkylhydroxylamine substrate by contacting the substrate with an aliphatic aldehyde or ketone, hydrogen and a hydrogenation catalyst, preferably a Raney Ni or Raney Co.

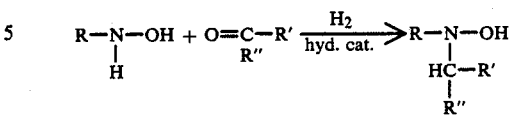

or alternately by hydrogenation of a nitrone to the corresponding N,N-dialkylhydroxylamine:

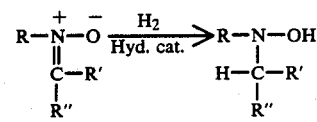

wherein, in each of the above instances R is an alkyl of 1-18 carbons, preferably 1-3; and R and R" are each independently H or alkyl of 1-10, preferably 1-4 carbons.

The in situ embodiment (equation I) avoids the necessity of recovering and starting with the pure nitrone, and is particularly desirable in that the byproducts of nitrone formation have been found not to interfere with the hydrogenation.

DETAILED DESCRIPTION OF THE INVENTION

The subject process requires the use of N-alkylhydroxylamine to form in situ a nitrone or the use of a previously formed nitrone. In each case, the reaction mixture is subjected to $H_2$ gas and contacted with a hydrogenation catalyst, preferably a Raney cobalt or Raney nickel.

The N-alkylhydroxylamine can be formed in known manners and used as the reactant to directly forming the desired product by reaction I.

The hydrogenation must be carried out using a hydrogenation catalyst. It has been found that any conventional hydrogenation catalyst will work to form a hydroxylamine when the compound is void of aryl groups. Examples of useful hydrogenation catalysts include Pd/C, Pd/Al$_2$O$_3$, Pt/C or Pt oxide, Ru/C, Rh/C and the like. The most preferred catalyst are Raney Co and Raney Ni as they provide good economic efficiency to the process of forming the desired product. Other Raney hydrogenation catalysts are also similarly useful including Raney aluminum and chromium promoted Raney cobalt and Raney nickel.

Hydrogen pressure can be in the range of about 15-200 psia, preferably 15-100 psia.

Reaction temperature can be in the range of about 0°-100° C., preferably about 15°-50° C.

Reaction time can be 0.5-50 hours, preferably 1-40 hours.

When the single vessel reaction is utilized, the mole ration of N-alkylhydroxylamine to aldehyde or ketone should be 1 to 0.2-5, preferably 1 to 0.5-1.5 and most preferably 1 to 1.

The following examples are given for illustrative purposes only and is not meant to be a limitation on the claimed invention, appended hereto. All parts are by weight unless otherwise indicated.

EXAMPLE 1

N-isopropyl, N-methylnitrone

To a sample of N-isopropylhydroxylamine, 39.3 g, 0.52 mole, there was first added 40 ml of a 5% sodium hydroxide solution and then 59 g of 37% formaldehyde solution, 0.73 mole. An exotherm to 41° C. occurred, with formation of the N-isopropyl, N-methylnitrone product.

EXAMPLE 2

N-isopropyl, N-methylhydroxylamine

An aliquot of the reaction mixture of Example 1 was placed in a 300 ml Hoke cylinder with 3.0 g of Raney cobalt catalyst (6 g of 50% slurry) and the cylinder was pressurized four times to a gauge pressure of 14.0 psi with hydrogen at 25° C. The total hydrogen consumed was equivalent to about 0.06 mole or about 45% of theory. The $^{13}$C NMR analyses of the final product indicated that the major product was N-isopropyl, N-methylhydroxylamine with minor amounts of unreacted nitrone and N-isopropyl, N-hydroxymethyl hydroxylamine present.

EXAMPLE 3

N-isopropyl, N-ethylnitrone

The procedure of Example 1 was followed, except that acetaldehyde was used instead of formaldehyde. N-isopropyl, N-ethylnitrone was formed in good yield.

EXAMPLE 4

N-isopropyl, N-ethylhydroxylamine

The reaction mixture resulting from Example 3 was hydrogenated, using the procedure of Example 2. The desired N-isopropyl, N-ethylhydroxylamine product was formed, as established by $^{13}$C NMR.

EXAMPLE 5

N,N-diisopropylnitrone

The procedure of Example 1 was followed, except that acetone was used instead of formaldehyde. N,N-diisopropylnitrone was formed in good yield.

EXAMPLE 6

N,N-diisopropylhydroxylamine

The reaction mixture resulting from Example 5 was hydrogenated, using the procedure of Example 2. The desired N,N-diisopropylhydroxylamine was formed, as established by $^{13}$C NMR.

EXAMPLE 7

N,N'-diethylhydroxylamine

To a sample of N-ethylhydroxylamine, 2.5 g, 0.040 moles, cooled to 0° C., was added 1.8 g, 0.040 moles, acetaldehyde. The reaction was rapidly completed. 0.87 g of this reaction product (comprising primarily the nitrone) was placed in a reaction flask along with 5 ml of MeOH and 23 mg of 5% pd/C. The reaction flask was put under 15 psia hydrogen and allowed to stir for 40 hours. At the end of this period, gas chromatography using an internal standard showed that N,N-diethylhydroxylamine was formed in 54% yield.

It will be noted that in Examples 1 and 2, R=isopropyl and R' and R''=H; in Examples 3 and 4, R=isopropyl, R'=H, and R''=methyl; in Examples 5 and 6, R=isopropyl and R' and R''=methyl; in Example 7, R=ethyl, R'=H, and R''=methyl.

EXAMPLE 8

N-isopropyl, N-methylhydroxylamine 39.3 grams of N-isopropylhydroxylamine, 40 ml of a 5% sodium hydroxide solution and 59 g of 37% formaldehyde solution are added to a 300 ml Hoke cylinder. After 2 hours the cylinder is charged with 3 g of Raney cobalt (6 g of a 50% slurry), sealed and pressurized four times to a gauge pressure of 14.0 psi with hydrogen gas at 25° C. The reaction mixture is allowed to remain in the cylinder for 16 hours. The final product is substantially the same as obtained in Example 2.

We claim:

1. Method of preparing an N,N-dialkyl hydroxylamine of the formula:

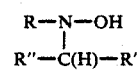

comprising reacting a nitrone of the formula:

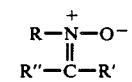

where R is alkyl of 1-18 carbons, and R' and R'' are each independently H or alkyl of 1-10 carbons, with hydrogen gas under hydrogen pressure of 15-200 psia and in the presence of a catalytic amount of a hydrogenation catalyst which is a number selected from the group consisting of Raney catalysts and Pd catalysts.

2. Method according to claim 1 wherein hydrogen pressure is about 15-100 psia; and said hydrogenation catalyst is a Raney catalyst.

3. Method according to claim 2 wherein the catalyst is Raney cobalt.

4. Method according to claim 1, 2, or 3 wherein R is isopropyl and R' and R'' are H.

5. Method according to claim 1, 2, or 3 wherein R is isopropyl, R' is H, and R'' is methyl.

6. Method according to claim 1, 2, or 3 wherein R is isopropyl and R' and R'' are methyl.

7. Method according to claim 1, 2, or 3 wherein R is ethyl, R' is H, and R'' is methyl.

8. Method according to claim 1, 2, or 3 wherein the nitrone reactant is formed in situ by reacting an N-alkyl-hydroxylamine of the formula R—N(H)—OH with a carbonyl compound of the formula O=C(R')R''.

* * * * *